United States Patent [19]

Winternitz et al.

[11] Patent Number: 4,792,616
[45] Date of Patent: Dec. 20, 1988

[54] DIARYL ETHERS

[75] Inventors: Paul Winternitz, Greifensee; René Zurflüh, Bülach, both of Switzerland

[73] Assignee: Hoffmann-La Roche Inc., Nutley, N.J.

[21] Appl. No.: 853,113

[22] Filed: Apr. 17, 1986

Related U.S. Application Data

[63] Continuation-in-part of Ser. No. 659,487, Oct. 10, 1984.

[30] Foreign Application Priority Data

Oct. 18, 1983 [CH] Switzerland ............... 5648/83
Aug. 17, 1984 [CH] Switzerland ............... 3946/84

[51] Int. Cl.$^4$ .................. C07C 79/46; A01N 37/38
[52] U.S. Cl. ................... 560/21; 546/301; 546/302; 546/312; 564/266; 564/265; 564/267; 71/116
[58] Field of Search .............. 560/21; 546/301, 302, 546/312; 564/266, 265, 267; 71/160

[56] References Cited

U.S. PATENT DOCUMENTS

| | | | |
|---|---|---|---|
| 3,137,563 | 6/1984 | Newcomer | 71/2.6 |
| 3,282,991 | 11/1966 | Klein et al. | 260/501 |
| 3,325,274 | 6/1967 | Anderson | 71/2.6 |
| 4,070,177 | 6/1978 | Nishiyama | 71/105 |
| 4,304,936 | 12/1981 | Rohr | 564/171 |

FOREIGN PATENT DOCUMENTS

| | | |
|---|---|---|
| EP34120 | 8/1981 | European Pat. Off. . |
| 0078536 | 5/1983 | European Pat. Off. . |
| 0089115 | 9/1983 | European Pat. Off. . |
| 58-150559 | 7/1983 | Japan . |

*Primary Examiner*—Paul J. Killos
*Attorney, Agent, or Firm*—Jon S. Saxe; George M. Gould; Dennis P. Tramaloni

[57] ABSTRACT

Novel diaryl ethers of the formula

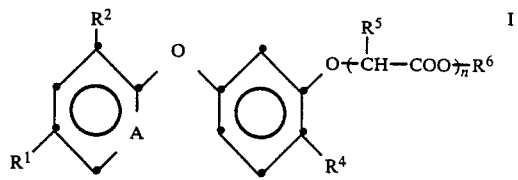

wherein A is $CR^3$ or N and $R^1$, $R^2$, $R^3$, $R^4$, $R^5$, n and $R^6$ are as defined hereinafter, processes for their preparation, herbicidal compositions which contain these compounds as the active ingredient as well as the use of these compounds or compositions for the control of weeds is disclosed.

35 Claims, No Drawings

DIARYL ETHERS

This application is a continuation-in-part of U.S. patent application Ser. No. 659,487, filed Oct. 10, 1984 now pending.

SUMMARY OF THE INVENTION

The invention is directed to diaryl ethers of the formula

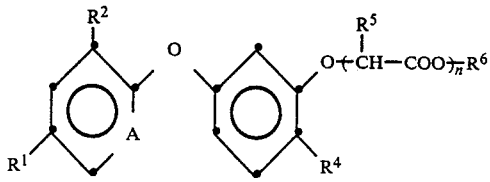

wherein A is $CR^3$ or N, $R^1$—$R^6$ and n are as defined hereinafter, and processes for their preparation. This invention is also directed to herbicidal compositions containing, as the active ingredient, a compound of formula I and methods for the use of these herbicidal compositions.

DETAILED DESCRIPTION OF THE INVENTION

The invention relates to diaryl ethers of the formula

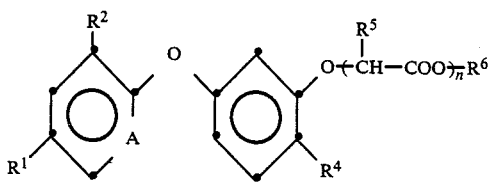

wherein
A is $CR^3$ or N,
$R^1$ is halogen or trifluoromethyl,
$R^2$ and $R^3$ independently of each other are hydrogen, halogen, nitro or cyano,
$R^4$ is halogen, nitro or cyano,
$R^5$ is hydrogen or $C_{1-3}$-alkyl.
n is 0 or 1.
$R^6$ is one of the following groups (a)–(c)

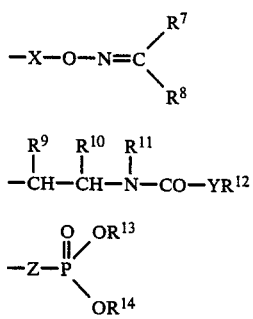

$R^7$ is $C_{1-6}$-alkyl,
$R^8$ is $C_{1-6}$-alkyl or $C_{1-6}$-alkoxy, or
$R^7$ and $R^8$ together with the carbon atom to which they are attached are a $C_{5-7}$-cycloalkane ring,
X is methylene, ethylene or ethylidene,
$R^9$ and $R^{10}$ independently of each other are hydrogen or $C_{1-4}$-alkyl,
$R^{11}$ is hydrogen or methyl,
$R^{12}$ is $C_{1-4}$-alkyl or 2-chloroethyl,
Y is oxygen or sulfur,
$R^{13}$ and $R^{14}$ independently of each other are $C_{1-6}$-alkyl and
Z is $C_{1-3}$-alkylene.

The invention is also directed to herbicidal compositions which contain, as the active ingredient, a compound of formula I, and methods for their use. The compounds have both preemergence and postemergence herbicidal activity.

In formula I above "halogen" encompasses fluorine, chlorine, bromine and iodine. The terms "$C_{1-3}$-alkyl", "$C_{1-4}$-alkyl" and "$C_{1-6}$-alkyl" encompass not only straight-chain but also branched alkyl groups such as methyl, ethyl, n-propyl, isopropyl, n-butyl, isobutyl, tert.butyl, n-pentyl, isoamyl, neo-pentyl and n-hexyl. This also applies to the alkyl portion of the $C_{1-6}$-alkoxy group. The term $C_{1-3}$-alkylene can also be straight-chain or branched, and thus means methylene, ethylene, ethylidene, 1- or 2-methylethylene, propylidene or trimethylene.

The presence of at least one asymmetric carbon atom in the compounds of formula I means that the compounds can occur in isomeric forms which are in enantiomeric or diastereomeric relationship to one another. The same applies to the compounds of formula I in which, in addition, $R^{13}$ and $R^{14}$ are different groups. The isomeric forms exhibit optical activity. Having regard to the presence of the nitrogen-carbon double bond in the compounds of formula I in which $R^6$ is a group (a), geometric isomerism additionally occurs for those compounds in which $R^7$ and $R^8$ represent different groups. Independently thereof, an atropic isomerism can also exist in certain cases. Accordingly, formula I is intended to embrace all of these possible isomeric forms.

An interesting sub-group of compounds of formula I comprises those compounds of formula I in which A is CH, $R^1$ is trifluoromethyl, $R^2$ is halogen, $R^4$ is halogen or nitro, $R^7$ and $R^8$ independently of each other are $C_{1-6}$-alkyl, $R^{12}$ is $C_{1-4}$alkyl and Y is oxygen.

Independently of one another A is preferably CH; $R^1$ is preferably trifluoromethyl; $R^2$ is preferably chlorine; $R^4$ is preferably nitro; $R^5$ is preferably hydrogen or methyl, especially methyl; and $R^7$ and $R^8$ are preferably methyl or ethyl.

Especially preferred compounds of formula I are:
Isopropylideneaminooxymethyl 2-[5-(o-chloro-p-trifluoromethyl-phenoxy)-2-nitrophenoxy]-propionate,
2-isopropylideneaminooxy-ethyl 2-[5-(o-chloro-p-trifluoromethyl-phenoxy)-2-nitrophenoxy]-propionate and
methyl N-{2-[2-[5-(o-chloro-p-trifluoromethyl-phenoxy)-2-nitrophenoxy]-propionyloxy]-ethyl}-N-methylcarbamate.

Further preferred compounds of formula I are:
Ethyl 2-[5-(o-chloro-p-trifluoromethyl-phenoxy)-2-nitrophenoxy]-ethylcarbamate,
ethyl 2-[2-[5-(o-chloro-p-trifluoromethyl-phenoxy)-2-nitrophenoxyl-propionyloxy]-ethylcarbamate and
diethyl [2-[5-(o-chloro-p-trifluoromethyl-phenoxy)-2-nitrophenoxy]-propionyloxy]methylphosphonate.

The compounds of formula I are prepared by one of the procedures described below.

(A) Reacting a phenol of the general formula

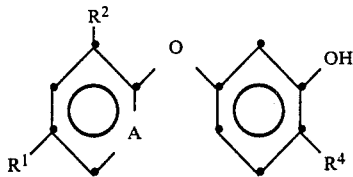

wherein A, $R^1$, $R^2$ and $R^4$ are as previously described, or an alkali metal salt thereof, with a compound of the general formula

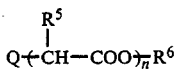   III wherein
$R^5$, n and $R^6$ are as previously described and
Q is a leaving group; or (B) Reacting an acid of the general formula

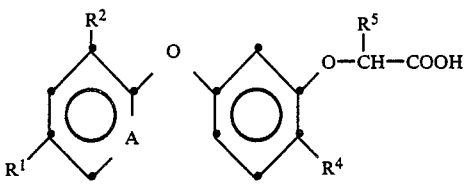   IV wherein A, $R^1$, $R^2$, $R^4$ 1 and $R^5$ are as previously described,
or a reactive derivative thereof, with a compound of the general formula $U-R^6$   V wherein $R^6$ are as previously described and U is hydroxy or a leaving group; or (C) Treating a compound of the general formula

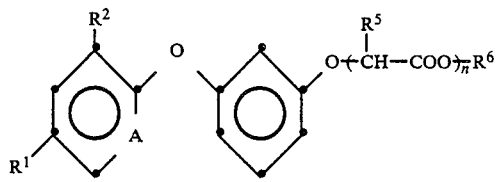   VI wherein A, $R^1$, $R^2$, $R^5$, n and $R^6$ are as previously described,
with a metal nitrate; or (D) Reacting a o-dinitrobenzene derivative of the general formula

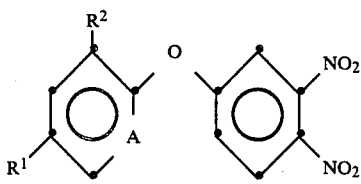   VII wherein A, $R^1$ and $R^2$ are as previously described, with an alcohol of the general formula

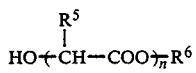   VIII wherein $R^5$, n and $R^6$ are as previously described, or an alkali metal salt thereof.

In procedure A the term "alkali metal salt" stands especially for the sodium, potassium or lithium salt of the respective phenol of formula II. The term "leaving group" for Q in formula III preferably stands for chlorine, bromine, iodine, mesyloxy or tosyloxy, or for a group $-N^{\oplus}R^{15}R^{16}R^{17}$ in which $R^{15}$, $R^{16}$ and $R^{17}$ independently of one another are hydrogen or lower alkyl or together with the nitrogen atom form a ring such as pyridinium, in which case halide, e.g. $Cl^{\ominus}$ or $Br^{\ominus}$, especially comes into consideration as a suitable anion. Where a compound of formula III in which Q is a group $-N^{\oplus}R^{15}R^{16}R^{17}$ is used as the starting material, the free phenol of formula II is used.

The reaction according to procedure A can be conveniently carried out by reacting an alkali metal salt of the phenol of formula II with a halide, especially the chloride, bromide or iodide, the mesylate or the tosylate of formula III in an inert organic solvent, especially a dipolar aprotic solvent such as dimethylformamide or dimethyl sulfoxide. The reaction temperature is not critical, and the reaction is generally carried out at temperatures between 0° C. and 120°, preferably between 20° C. and 70° C. As a preliminary step the phenol of formula II is converted into the alkali metal salt, preferably using sodium hydride or potassium hydroxide with azeotropic removal of water.

The reaction according to procedure A can also be conveniently carried out by reacting the free phenol of formula II with a halide, especially the chloride, bromide or iodide, the mesylate or the tosylate of formula III in the presence of a suitable inorganic base, e.g. an alkali metal or alkaline earth metal carbonate or bicarbonate, or an organic base such as a tert. amine, e.g. triethylamine, dimethylaniline, pyridine or, especially, 1,8-diaza-bicyclo[4,5,0]undec-7-ene. Moreover, the reaction is conveniently carried out in a polar aprotic solvent such as an aliphatic ketone, e.g. acetone or 2-butanone, dimethylformamide or acetonitrile and optionally in the presence of a catalytic amount of sodium iodide, potassium iodide or a quaternary ammonium iodide, e.g. tetrabutylammonium iodide. The reaction is conveniently carried out at temperatures between 0° C. and 150° C., preferably between 20° C. and 100° C.

If in procedure A Q in formula III is a group $-N^{\oplus}R^{15}R^{16}R^{17}$, as described more precisely above, then the reaction is preferably carried out in a medium containing hydroxyl groups, e.g. in the presence of sodium or potassium hydroxide. The reaction with the free phenol of formula II is conveniently carried out in an inert organic diluent such as an aromatic hydrocarbon, e.g. toluene, an aliphatic or cyclic ether, e.g. dimethoxyethane or dioxan, an aprotic dipolar solvent, e.g. dimethylformamide or acetonitrile, or a mixture of such diluents. The reaction is conveniently carried out at temperatures between 70° C. and 160° C., preferably between 100° C. and 120° C.

Procedure B, which leads to those compounds of formula I in which n signifies 1, is an esterification which can be carried out according to methods known per se. Therefore, the term "reactive derivative" is especially a halide, the imidazolide or the anhydride of the pertinent acid of formula IV. Preferred leaving groups U in formula V are chlorine, bromine, iodine, mesyloxy and tosyloxy, further a group —N⊕R$^{15}$R$^{16}$R$^{17}$ as is described in more detail in connection with procedure A.

The esterification of a free acid of formula IV with a compound of formula V in which U is a leaving group such as chlorine, bromine, iodine, mesyloxy or tosyloxy is conveniently carried out in the presence of a base or of an acid acceptor. For this purpose there can be used all customarily usable inorganic and organic acid-binding agents, but preferably alkali metal and alkaline earth metal carbonates and bicarbonates, and tertiary amines, e.g. triethylamine, dimethylaniline, 1,8-diaza-bicyclo[4,5,0]undec-7-ene and pyridine. The reaction is conveniently carried out in an inert diluent, preferably an inert organic solvent such as an aliphatic or cyclic ether, e.g. diethyl ether or tetrahydrofuran, a hydrocarbon, e.g. n-hexane, benzene or toluene, an aliphatic ketone, e.g. acetone or 2-butanone, a chlorinated hydrocarbon, e.g. dichloromethane, chloroform or carbon tetrachloride, or a dipolar aprotic solvent, e.g. dimethylformamide, dimethyl sufoxide, N-methylpyrrolidone, sulfolane or hexamethylphosphoric acid triamide. The reaction is carried out at tempeatures between room temperature and the reflux tempeature of the reaction mixture.

The esterification of a free acid of formula IV with a compound of formula V in which U signifies a group —N⊕R$^{15}$R$^{16}$R$^{17}$ as the leaving group is preferably carried out in a medium containing hydroxyl groups, e.g. in the presence of sodium or potassium hydroxide. The reaction is conveniently carried out in an inert organic diluent such as an aromatic hydrocarbon, e.g. toluene, an aliphatic or cyclic ether, e.g. dimethoxyethane or dioxan, an aproptic dipolar solvent, e.g. dimethylformamide or acetonitrile or a mixture of such diluents at temperatures between 70° C. and 160° C., preferably between 100° C. and 120° C.

The reaction of a free acid of formula IV with a compound of formula V in which U is hydroxy is conveniently carried out in an inert organic diluent such as an aliphatic or cyclic ether, e.g. diethyl ether, diisopropyl ether, 1,2-dimethoxyethane, tetrahydrofuran or dioxan, a chlorinated hydrocarbon, e.g. dichloromethane, chloroform, carbon tetrachloride or trichloroethane, or an aromatic hydrocarbon, e.g. benzene, toluene or a zylene, and at temperatures between 0° C. and the reflux temperature of the reaction mixture. Moreover, the reaction is conveniently carried out in the presence of an acidic catalyst or of a condensing agent such as sulfuric acid, hydrochloric acid, p-toluenesulfonic acid, dicyclohexylcarbodiimide or carbonyldiimidazole. Carbonyldiimidazole is preferably used as the condensing agent, in which case the reaction is preferably carried out in the presence of an ether as the diluent. If the acid of formula IV is used, it is dissolved or suspended e.g. in an inert organic diluent, especially in aliphatic or cyclic ether, and the solution or suspension is added to a solution or suspension of carbonyldiimidazole in the same diluent. After the resulting evolution of carbon dioxide is complete, the mixture is treated with a solution of the alcohol of formula V which has previously been treated with a catalytic amount of sodium or sodium hydride until the evolution of hydrogen has finished. The reaction is preferably carried out in a temperature range between room temperature and about 50° C.; it is normally finished within about 2 hours.

Where a reactive derivative of an acid of formula IV is reacted with a compound of formula V, U in the latter formula stands for hydroxy. The reaction is conveniently carried out in an inert diluent such as an aliphatic or cyclic ether, e.g. diethyl ether or tetrahydrofuran, a hydrocarbon, e.g. n-hexane, benzene or toluene, or a chlorinated hydrocarbon, e.g. dichloromethane, chloroform or carbon tetrachloride, and at room temperature or elevated temperature, e.g. up to the reflux temperature of the reaction mixture.

When an acid halide of the acid of formula IV is used the reaction is conveniently carried out in the presence of an acid-binding agent and preferably at temperatures between 0° C. and 40° C., especially between 0° C. and 10° C. Suitable acid-binding agents are inorganic bases, e.g. alkali metal and alkaline earth metal carbonates and bicarbonates, as well as organic bases, e.g. tertiary amines, especially triethylamine or pyridine. The acid chloride is the preferred acid halide. When the anhydride of the acid of formula IV is used the reaction is conveniently carried out in the presence of an acid-binding agent, especially an organic base such as a tertiary amine, e.g. triethylamine, dimethylaniline or pyridine, at temperatures between 0° C. and 40° C., especially at room temperature, or in the absence of an acid-binding agent at elevated temperature.

In the case of procedure C, which leads to those compounds of formula I in which R$^4$ is nitro, the term "metal nitrate" encompasses copper(II), iron(III), cobalt(II), cobalt(III), nickel(III), chromium(III), manganese(II) or aluminium(III) nitrate. Copper(II), iron(III) and aluminium(III) nitrate are the preferred metal nitrates. The reaction is conveniently carried out in the presence of acetic anhydride and an inert diluent, especially an organic solvent, and at temperatures between 0° C. and 100° C., especially between 10° C. and 50° C. Acetic anhydride is preferably used as the diluent. The reaction is preferably carried out with an excess of metal nitrate, generally with a 1 to 10 molar excess, preferably a 1.0 to 1.5 molar excess, of metal nitrate. These procedures are described e.g. by J. B. Menke in Rec. Trav. Chim. Pays-Bas 44, 141 and 269 (1925), by G. Bacharach in J. Amer. Chem. Soc. 49, 1522 (1927) and by A. M. Talati and B. Shah in Ind. J. Chem. 11, 1076 (1973).

Procedure D also leads to those compounds of formula I in which R$^4$ is nitro. Under the term "alkali metal salt" of the alcohol of formula VIII there is to be understood in particular the sodium, potassium or lithium salt. The reaction is conveniently carried out in an inert diluent, especially an organic solvent such as tetrahydrofuran or dioxan, and in the presence of a base such as an alkali metal hydroxide, e.g. sodium or potassium hydroxide. The reaction is generally carried out in a temperature range between room temperature and the reflux temperature, preferably between 40° C. and 100° C. Such a process is described e.g. in German Offenlegungsschrift No. 2,926,829.

The product obtained can be isolated and purified according to conventional methods well known to those skilled in the art.

Insofar as no planned synthesis for the isolation of pure isomers is carried out, the product normally occurs as a mixture of two or more isomers. The isomers can be separated according to methods well known in the art.

If desired, they can also be manufacture by synthesis from corresponding optically active starting materials.

The starting materials of formulae II and IV as well as their alkali metal salts or reactive derivatives are either known or can be produced in a manner known per se. The compounds of formula III used as starting materials in procedure A, which also embrace the starting materials of formula V in which U is a leaving group used in procedure B, can be prepared in a manner known per se, e.g. in accordance with the following Reaction Scheme:

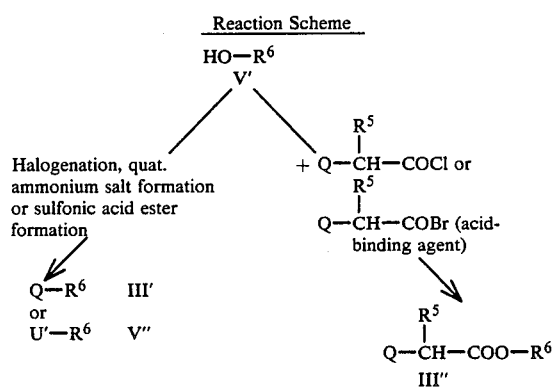

In the above Reaction Scheme $R^5$, $R^6$ and Q are as previously described; U' is a leaving group, especially chlorine, bromine, iodine, mesyloxy or tosyloxy, or a group $-N^{\oplus}R^{15}R^{16}R^{17}$ as described in more detail in connection with procedure A. The reaction conditions are well known to a person skilled in the art.

The remaining starting materials of formula V, i.e. those compounds of formula V in which U is hydroxy and the above compounds of formula V', are either known or can be prepared in a manner known per se.

The starting materials of formula VI can be prepared by reacting a phenol of the general formula

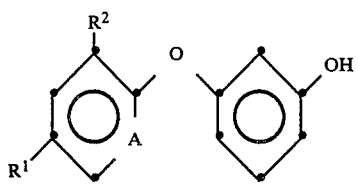

wherein A, $R^1$ and $R^2$ are as previously described, or an alkali metal salt thereof, such as the sodium, potassium or lithium salt, with a compound of general formula III given above. The reaction is conveniently carried out under those reaction conditions which are described above in connection with procedure A.

The o-dinitrobenzene derivatives of formula VII used as starting materials in procedure D can be produced analogously to the process for the preparation of 1-(2-chloro-4-trifluoromethyl-phenoxy)-3,4-dinitrobenzene described in German Offenlegungsschrift No. 2,926,829.

The alcohols of formula VIII and their alkali metal salts used as starting materials in procedure D can be prepared in a manner known per se, e.g. by reacting an alcohol of general formula V' given above with an acid chloride of the formula

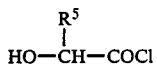

wherein $R^5$ is as previously described, in the presence of an acid-binding agent, and optional subsequent alkali metal salt formation.

The compounds of formula I are useful as both pre-emergent and postemergent herbicides. They are particularly suitable for the control of weeds, especially of monocotyledonous weed grasses such as corn millet (*Sorghum bicolor*), cock's foot (*Echinochloa crus-galli*) and finger millet (Digitaria spp.), as well as dicotyledonous weed grasses such as Chinese hemp (*Abutilon theophrasti*), white goosefoot (*Chenopodium album*), hirsute amaranth (*Amaranthus retroflexus*), charlock (*Sinapis arvensis*), thorn apple (*Dature stramonium*), morning glory (Ipomoea spp) and cocklebur (*Xanthium pensylvanicum*) in diverse crops, especially in rice and cereal crops.

In general, the compounds of formula I are effective as herbicides when applied at a concentration of about 0.01 to about 3kg/ha with the preferred concentration range being from about 0.01 to about 1 kg/ha.

This invention is also directed to herbicidal compositions which comprise inert carrier material and, as the active ingredient, one or more compounds of formula I. These herbicidal compositions suitably contain, as the inert carrier material, at least one of the following ingredients: solid carrier materials, solvents or dispersion media, tensides (wetting and emulsifying agents), dispersing agents (without tenside action) and stabilizers. The herbicidal compositions of this invention can be formulated in the usual forms, for example dusts, powders, granulates, solutions, emulsions, suspensions, emulsifiable concentrates, pastes, and the like.

The compounds of formula I are in general water-insoluble. Thus, the usual methods of formulation of insoluble materials can be employed. For example, the compounds can be mixed with solid carrier substances, dissolved or suspended in suitable solvents or dispersion media, if necessary using tensides as wetting or emulsifying agents and/or dispersing agents, diluting prepared emulsifiable concentrates with solvents or dispersion media, etc.

Suitable solid carrier materials include natural mineral substances, such as chalk, dolomite, limestone, aluminas, and silicic acid and salts thereof, for example, siliceous earth, kaolin, bentonite, talc, attapulgite and montmorillonite; synthetic mineral substances, such as highly dispersible silicic acid, aluminium oxide and silicates; organic substances, such as cellulose, starch, urea and synthetic resins; and fertilizers, such as phosphates and nitrates. The solid carrier substances can be present as powders or as granulates.

Suitable solvents or dispersion media include aromatic hydrocarbons, such as benzene, toluene, xylenes and alkylnaphthalenes; chlorinated aromatic and chlorinated aliphatic hydrocarbons, such as chlorobenzenes, chloroethylenes and methylene chloride; aliphatic hydrocarbons, such as cyclohexane and paraffins, for example, petroleum fractions; alcohols, such as butanol and glycol, as well as their ethers and esters; ketones, such as acetone, methyl ethyl ketone, methyl isobutyl ketone and cyclohexanone; and strongly polar solvents or dispersion media such as dimethylformamide, N-methylpyrrolidone and dimethyl sulfoxide, whereby such solvents or dispersion media preferably have flash points of at least 30° C. and boiling points of at least 50° C., and water. Also included in the solvents or dispersion media which can be used in preparing the herbicidal compositions are the socalled liquified gaseous extenders or carrier substances, these being products which are gaseous at room temperature and under normal pressure. Examples of such products are aerosol propellant gases such as halogenated hydrocarbons, for example, dichlorodifluoromethane. If a weed control composition in accordance with the invention is present in the form of a pressurized pack, then a solvent is conveniently used in addition to the propellant gas.

Tensides (wetting and emulsifying agents) suitable for use with the compounds of this invention can be anionic, cationic or nonionic.

Examples of anionic tensides include soaps; fatty sulfate esters, such as dodecyl sodium sulfate, octadecyl sodium sulfate and cetyl sodium sulfate; alkyl sulfonates, aryl sulfonates and fatty-aromatic sulfonates, such as alkylbenzene-sulfonates, for example, calcium dodecylbenzene sulfonate, and butylnaphthalene-sulfonates; and the more complex fatty sulfonates, such as the amide condensation products of oleic acid and N-methyltaurine or the sodium sulfonate of dioctyl succinate.

Examples of nonionic tensides include, for example, condensation products of fatty acids, fatty alcohols or fatty-substituted phenols with ethylene oxide; fatty acid esters and ethers of sugars or polyhydric alcohols; condensation products of sugars or polyhydric alcohols with ethylene oxide; block copolymers of ethylene oxide and propylene oxide, or alkyldimethylamine oxides.

Examples of cationic tensides include alkyldimethyl-benzylammonium chlorides, dialkyldimethylammonium chlorides, alkyltrimethylammonium chlorides and ethoxylated quaternary ammonium chlorides.

Suitable dispersing agents (without tenside action) include lignin, sodium and ammonium salts of lignin sulphonic acids, sodium salts of maleic acid anhydride/-diisobutylene copolymers, sodium and ammonium salts of sulphonated polycondensation products of naphthalene and formaldehyde, and sulfite lyes.

Dispersing agents which are especially suitable as thickening agents or antisettling agents include methyl-cellulose, carboxymethylcellulose, hydroxyethylcellulose, polyvinyl alcohol, alginates, caseinates and blood albumin.

Examples of suitable stabilizers are acid-binding agents, for example, epichlorohydrin, phenyl glycidyl ether, soya epoxides and the like; antioxidants, for example, gallic acid esters, butylhydroxytoluene and the like; UV-absorbers, for example, substituted benzophenones, diphenylacrylonitrile acid esters, cinnamic acid esters and the like; and deactivators, for example, salts of ethylenediaminotetraacetic acid, polyglycols and the like.

The herbicial compositions of this invention can also contain, in addition to the compounds of formula I, synergistic agents and other active ingredients, such as insecticides, acaricides, bactericides, other herbicides, fungicides, plant growth regulators and fertilizers. Such combination preparations are suitable for increasing the activity or for broadening the spectrum of activity.

The herbicidal compositions of this invention generally contain between 0.001 and 95 precent by weight, preferably between 5 and 75 percent by weight, of one or more compounds of formula I as the active ingredient. The composition can be in the form of emulsifiable concentrates suitable for storage and shipment. In such concentrate formulations the active substance concentration is normally in the higher range, preferably between 10 and 75 percent by weight, especially between 25 and 50 percent by weight. These formulations can subsequently be diluted, for example, with the same or different inert ingredients, to give active ingredient concentrations which are suitable for practical use, i.e. preferably about 0.1 and 10 percent by weight, especially about 1 to 5 percent by weight. The active ingredient concentrations can, however, also be smaller or greater.

The herbicidal compositions of this invention can be prepared according to known formulation procedures.

For the preparation of pulverous preparations, the active ingredient, i.e. at least one compound of formula I, can be mixed with solid carrier materials, for example, by grinding the ingredients together, or the solid carrier material can be impregnated with a solution or suspension of the active ingredient and then the solvent or dispersion medium can be removed by evaporation, heating, or by evaporation under reduced pressure. By adding tensides or dispersing agents, such pulverous preparations can be made readily wettable with water, so that they can be converted into aqueous suspensions which are suitable, for example, as spray compositions.

The compounds of formula I can also be mixed with a tenside and a solid carrier material to form a wettable powder which is dispersible in water, or they can be mixed with a solid pre-granulated carrier material to form a granulate.

If desired, the compounds of formula I can be dissolved in a water-immiscible solvent, such as, for example, a high-boiling hydrocarbon, which conveniently contains a dissolved emulsifying agent, so that the solution becomes self-emulsifying upon addition to water. Alternatively, the active ingredient can be mixed with an emulsifying agent, and the mixture can then be diluted with water to the desired concentration. Moreover, the active ingredient can be dissolved in a solvent, and thereafter the solution can be mixed with an emulsifying agent. Such a mixture can likewise be diluted with water to the desired concentration. In this matter there are obtained emulsifiable concentrates or ready-for-use emulsions.

The use of the herbicidal compositions of this invention can be carried out according to usual application methods, such as sprinkling, spraying, dusting, pouring or scattering. The method of this invention for the control of weeds comprises treating the locus to be protected against weeds and/or the weeds with a compound of formula I or with a herbicidal composition in accordance with the invention.

The following Examples illustrate the invention in more detail.

I.

Preparation of the active ingredient compounds of formula I

EXAMPLE 1

4.2 g of silver oxide are added to a solution of 3.0 g of diethyl-methyl-isopropylideneaminooxymethyl-ammonium iodide in 10 ml of methanol and the mixture is stirred in the dark for 1 hour at room temperature. The solid constituents are filtered off and 3.0 g of 5-(o-chloro-p-trifluoromethyl-phenoxy)-2-nitrophenol as well as 50 ml of toluene are added to the filtrate. After azeotropically distilling off the methanol and the water formed in the reaction the mixture is heated at reflux temperature for 15 minutes, cooled and poured into 100 ml of water. The organic phase is separated and the aqueous phase is extracted with 50 ml of ethyl acetate. The combined organic phases are subsequently washed in succession with 100 ml of 2N hydrochloric acid, with 100 ml of 5% sodium bicarbonate solution and twice with 100 ml of water each time. The solvent is evaporated and the residue is purified by chromatography on a ten-fold amount of silica gel using diethyl ether/n-hexane (1:9) as the eluant. There is obtained 2-propanone O-[[5-(o-chloro-p-trifluoromethylphenoxy)-2-nitrophenoxy]methyl]oxime as a colourless oil (2.9 g), $n_D^{20}$ 1.5443; mass spectrum m/e 418; $^1$H-NMR (CDCl$_3$; 60 MHz) 7.90 ppm (d, 1H), 7.80 ppm (d, 1H), 7.65 ppm (dd, 1H), 7.25 ppm (d, 1H), 6.65 ppm (dd, 1H), 5.70 ppm (s, 2H), 1.78 ppm (d, 6H).

EXAMPLE 2

A solution of 1.65 of diethyl-methyl-isopropylideneaminooxymethyl-ammonium iodide in 10 ml of methanol is stirred in the dark for 1 hour at room temperature in the presence of 2.3 g of silver oxide. The solid constituents are filtered off, 2.0 g of 2-[5-(o-chloro-p-trifluoromethyl-phenoxy)-2-nitrophenoxy]-propionic acid as well as 50 ml of toluene are added to the filtrate and the methanol and the water formed are distilled off azeotropically. The mixture is thereafter heated at reflux temperature for a half hour, cooled and poured into 100 ml of water. The organic phase is separated and the aqueous phase is extracted twice with 50 ml of ethyl acetate each time. The combined organic phases are subsequently washed in succession with 50 ml of 2N hydrochloric acid, with 50 ml of 5% sodium bicarbonate solution and twice with 50 ml of water each time. The solvent is evaporated and the residue is purified by chromatography on a ten-fold amount of silica gel using n-hexane/ethyl acetate (1:1) as the eluant. There is obtained isopropylideneaminooxymethyl 2-[5-(o-chloro-p-trifluoromethyl-phenoxy)-2-nitrophenoxy]-propionate, $n_D^{20}$ 1.5346; mass spectrum m/e 490; $^1$H-NMR (CDCl$_3$; 60 MHz) 7.90 ppm (d, 1H), 7.80 ppm (d, 1H), 7.60 ppm (dd, 1H), 7.20 ppm (d, 1H), 6.60 ppm (d, 1H), 6.55 ppm (dd, 1H), 5.75 ppm (s, 2H), 4.75 ppm (q, 1H), 1.90 ppm (d, 6H), 1.72 ppm (d, 6H).

EXAMPLE 3

A solution of 4.0 g of 5-(o-chloro-p-trifluoromethyl-phenoxy)-1-nitrophenol in 30 ml of acetonitrile is heated at reflux temperature for 1 hour with 2.0 g of potassium carbonate. After the addition of catalytic amounts of potassium iodide and tetrabutylammonium iodide a solution of 1.9 g of methyl 2-chloro-ethylcarbamate in 15 ml of acetonitrile is added dropwise to the warm mixture and the reaction mixture is held at reflux temperature for 35 hours. The cooled reaction mixture is filtered and the filtrate is diluated with diethyl ether. The ether solution is washed with 2N hydrochloric acid, water and saturated sodium chloride solution, dried over anhydrous sodium sulphate and evaporated under reduced pressure. The oily residue is purified by chromatography on silica gel with n-hexane/ethyl acetate (4:1). There is obtained methyl 2-[5-(o-chloro-p-trifluoromethyl-phenoxy)-2-nitrophenoxy]-ethylcarbamate, m.p. 91°–92° C.

In an analogous manner, using ethyl 2-chloro-ethylcarbamate there is obtained ethyl 2-[5-(o-chloro-p-trifluoromethyl-phenoxy)-2-nitrophenoxy]-ethylcarbamate, m.p. 70°–71° C.

EXAMPLE 4

2.0 g of 5-(o-chloro-p-trifluoromethyl-phenoxy)-2-nitrophenol and 1.0 g of potassium carbonate are heated at reflux temperature for 15 minutes in 30 ml of acetonitrile. A solution of 1.68 g of methyl 2-(2-bromopropionyloxy)-ethylcarbamate in 10 ml of acetonitrile is then added dropwise thereto during 5 minutes and the mixture is left to react at reflux temperature for about 16 hours. For the working-up, the mixture is poured on to ice-water and extracted twice with diethyl ether. The combined ether solutions are washed with 2N hydrochloric acid, water and saturated sodium chloride solution, dried over anhydrous sodium sulphate and evaporated. The oily residue is purified by chromatography on silica gel with n-hexane/ethyl acetate (4:1). There is obtained methyl 2-[2-[5-(o-chloro-p-trifluoromethyl-phenoxy)-2-nitrophenoxy]-propiony], $n_D^{20}$ 1.5258.

In an analogous manner, by using ethyl 2-(2-bromopropionyloxy)-ethylcarbamate there is obtained ethyl 2-[2-[5-(o-chloro-p-trifluoromethyl-phenoxy)-2-nitrophenoxy]-propionyloxy]-ethylcarbamate, $n_D^{24}$ 1.5185;

by using methyl 2-bromoacetoxy-ethylcarbamate there is obtained methyl 2-[[5-(o-chloro-p-trifluoromethyl-phenoxy)-2-nitrophenoxy]-acetoxy]-ethylcarbamate, m.p. 105°–108° C.;

by using ethyl 2-bromoacetoxy-ethylcarbamate there is obtained ethyl 2-[[5-(o-chloro-p-trifluoromethyl-phenoxy)-2-nitrophenoxy]-acetoxy]-ethylcarbamate, m.p. 94°–95° C.;

by using methyl 2-(2-bromopropionyloxy)-propylcarbamate there is obtained methyl 2-[2-[5-(o-chloro-p-trifluoromethyl-phenoxy)-2-nitrophenoxy]-propionyloxy]-propylcarbamate $^1$H-NMR (CDCl$_3$, 60 MHz) 8.1–6.46 ppm (m, 6H) 5.23–4.63 ppm (m, 2H), 4.83 ppm (q, 1H), 3.65 ppm (s, 3H), 3.5–3.13 ppm (m, 2H), 1.70 ppm (d, 3H), 1.23 ppm (d, 3H);

by using ethyl 1-ethyl-2-(2-bromopropionyloxy)-ethylcarbamate there is obtained ethyl 1-ethyl-2-[2-[5-(o-chloro-p-trifluoromethyl-phenoxy)-2-nitrophenoxy]-propionyloxy]-ethylcarbamate, $^1$H-NMR (CDCl$_3$, 400 MHz) 7.91 ppm (d, 1H), 7.79 ppm (dd, 1H), 7.61–7.56 ppm (m, 1H), 7.20 ppm (dd, 1H), 6.67 ppm (broad s, 1H) and 6.59 ppm (d, 1H), 6.51 ppm (dd, 1H), 4.85 ppm (q, 1H), 4.73–4.53 ppm (m, 1H), 3.85–3.71 ppm (m, 1H), 1.7 and 1.695 ppm (2d, 3H), 1.56–1.3 ppm (m, 2H), 1.29–1.18 ppm (m, 3H), 0.93 and 0.90 ppm (2t, 3H);

by using isobutyl 2-(2-bromopropionyloxy)-ethylcarbamate there is is obtained isobutyl 2-[2-[5-(o-chloro-p-trifluoromethyl-phenoxy)-2-nitrophenoxy]-propionyloxy]-ethylcarbamate, $^1$H-NMR (CDCl$_3$, 60 MHz) 8.1–6.4 ppm (m, 6H), 5.17–4.80 ppm (broad s, 1H), 4.86 ppm (q, 1H), 4.23 ppm (t, 2H), 3.80 ppm (d, 2H), 3.66–3.26 ppm (m, 2H), 1.70 ppm (d, 3H), 1.90 ppm (m, 1H), 0.93 ppm (d, 6H);

by using methyl N-[2-(2-bromopropionyloxy)-ethyl]-N-methyl-carbamate there is obtained methyl N-{2-[2-[5-(o-chloro-p-trifluoromethyl-phenoxy)-2-nitrophenoxy]-propionyloxy]-ethyl}-N-methyl-carbamate, $^1$H-NMR (CDCl3, 60 MHz) 8.1–6.43 ppm (m, 6H), 4.83 ppm (q, 1H), 4.26 ppm (t, 2H), 3.67 ppm (s, 3H), 3.50 ppm (t, 2H), 2.86 ppm (s, 3H), 1.68 ppm (d, 3H).

In an analogous manner, using 5-(o-chloro-p-trifluoromethyl-phenoxy)-2-chlorophenol and:

methyl 2-(2-bromopropionyloxy)-ethylcarbamate there is obtained methyl 2-[2-[5-(o-chloro-p-trifluoromethyl-phenoxy)-2-chlorophenoxy]-propionyloxy]-ethylcarbamate, ¹H-NMR (CDCl₃, 60 MHz) 7.85–6.45 ppm (several signals, 6H), 5.05 ppm (t, 1H), 4.83 ppm (q, 1H, γ=about 7–8 Hz), 4.39–3.85 ppm (several signals, 4H), 3.65 ppm (s, 3H), 1.70 ppm (d, 3H, γ=about 7–8 Hz);

ethyl 2-(2-bromopropionyloxy)-ethylcarbamate there is obtained ethyl 2-[2-[5-(o-chloro-p-trifluoromethyl-phenoxy)-2-chlorophenoxy]-propionyloxy]-ethylcarbamate; ¹H-NMR (CDCl₃, 60 MHz) 7.85–6.45 ppm (several signals, 6H), 5.0 ppm (t, 1H), 4.85 ppm (q, 1H, γ=about 7–8 Hz), 4.40–3.90 ppm (several signals, 4H), 3.42 ppm (q, 2H, γ=about 7–8 Hz), 1.72 ppm (d, 3H, γ=about 7–8 Hz), 1.25 ppm (t, 3H, γ=about 7–8 Hz);

2-isopropylideneaminooxy-ethyl 2-bromopropionate there is obtained 2-isopropylideneaminooxy-ethyl 2-[5-(o-chloro-p-trifluoromethyl-phenoxy)-2-chlorophenoxy]-propionate, ¹H-NMR (CDCl₃, 60 MHz) 7.85–6.45 ppm (several signals, 6H), 4.80 ppm (q, 1H, γ=about 7–8 Hz), 4.30 ppm (m, 4H), 1.80 ppm (s, 3H), 1.78 ppm (s, 3H), 1.70 ppm (d, 3H, γ=about 7–8 Hz).

EXAMPLE 5

1.3 g of D-2-[5-(o-chloro-p-trifluoromethyl-phenoxy)-2-nitrophenoxy]-propionic acid are heated at reflux temperature for 1 hour with 15 ml of thionyl chloride. The excess thionyl chloride is then distilled off at reduced pressure and the residue is dried in a high vacuum. After the addition of 10 ml of methylene chloride and 0.27 g of pyridine 0.47 g of ethyl 2-hydroxyethylcarbamate in 10 ml of methylene chloride is added dropwise thereto at 0°–5° C. and the mixture is left to react at room temperature for about 16 hours. For the working-up, the mixture is poured into water and extracted three times with diethyl ether. The extracts are washed with 2N hydrochloric acid, water and saturated sodium chloride solution, dried over anhydrous sodium sulphate and evaporated. By chromatography on silica gel with n-hexane/ethyl acetate (4:1) there is obtained ethyl 2-[D-2-[5-(o-chloro-p-trifluoromethyl-phenoxy)-2-nitrophenoxy]-propionyloxy]-ethylcarbamate, $n_D^{20}$ 1.5362; $[\alpha]_D^{22}$ −18.85° (c=1.15% in CHCl₃).

In an analagous manner, by using D-2-[5-(o-chloro-p-trifluoromethyl-phenoxy)-2-nitrophenoxy]-propionic acid and methyl 2-hydroxyethylcarbamate there is obtained methyl 2-[D-2-[5-(o-chloro-p-trifluoromethyl-phenoxy)-2-nitrophenoxy]-propionyloxy]-ethylcarbamate, $[\alpha]_D^{20}$ −15.76° (c=0.83% in CHCl₃); ¹H-NMR (CDCl₃, 60 MHz) 8.1–6.45 ppm (m, 6H), 5.26–4.7 ppm (broad s, 1H), 4.88 ppm (q, 1H), 4.25 ppm (t, 2H), 3.70 ppm (s, 3H), 3.67–3.28 ppm (m, 2H), 1.73 ppm (d, 3H).

EXAMPLE 6

0.41 g of pyridine is added dropwise at room temperature to a solution of 2.0 g of DL-2-[5-(o-chloro-p-trifluoromethyl-phenoxy)-2-nitrophenoxy]-propionyl chloride and 0.86 g of diethyl 2-hydroxyethylphosphonate in 5 ml of methylene chloride. The reaction mixture is stirred at room temperature for 1 hour and subsequently evaporated to dryness under reduced pressure. The residue is dissolved in ethyl acetate and the solution is washed with water, dried over anhydrous sodium sulphate and evaporated to dryness. The residue is purified by chromatography on silica gel with ethyl acetate/n-hexane (1:1). There is obtained diethyl 2-[DL-2-[5-(o-chloro-p-trifluoromethylphenoxy)-2-nitrophenoxy]-propionyloxy]-ethylphosphonate, ¹H-NMR (CDCl₃; 400 MHz) 7.93 ppm (d, 1H), 7.79 ppm (d, 1H), 7.59 ppm (q, 1H), 7.21 ppm (d, 1H), 6.62 ppm (d, 1H), 6.51 ppm (q, 1H), 4.81 ppm (q, 1H), 4.39 ppm (m, 2H), 4.11 ppm (m, 4H), 2.12 ppm (m, 1H), 1.71 ppm (d, 3H), 1.33 ppm (tt, 6H).

In an analogous manner, by using 5-(o-chloro-p-trifluoromethyl-phenoxy)-2-nitrophenoxy-acetyl chloride and diethyl 2-hydroxyethylphosphonate there is obtained diethyl 2-[[5-(o-chloro-p-trifluoromethyl-phenoxy)-2-nitrophenoxy]acetoxy]-ethylphosphonate, ¹H-NMR (CDCl₃, 400 MHz) 7.96 ppm (d, 1H), 7.80 ppm (d, 1H), 7.59 ppm (q, 1H), 7.21 ppm (d, 1H), 6.71 ppm (d, 1H), 6.52 ppm (q, 1H), 4.78 ppm (s, 2H), 4.45 ppm (m, 2H), 4.12 ppm (m, 4H), 2.17 ppm (m, 2H), 1.33 ppm (tt, 6H);

by using 2-[5-(o-chloro-p-trifluoromethyl-phenoxy)-2-nitrophenoxy]-propionyl chloride and diethyl 1-hydroxyethylphosphonate there is obtained diethyl 1-[2-[5-(o-chloro-p-trifluoromethyl-phenoxy)-2-nitrophenoxy]-propionyloxy]-ethylphosphonate, ¹H-NMR (CDCl₃, 400 MHz) 7.93 ppm and 7.92 ppm (2d, 1H), 7.79 ppm (d, 1H), 7.51–7.55 ppm (m, 1H), 7.23 ppm and 7.19 ppm (2d, 1H), 6.68 ppm and 6.58 ppm (2d, 1H), 6.53 ppm and 6.46 ppm (2q, 1H), 5.31 ppm and 5.29 ppm (2q, 1H), 4.88 and 4.85 ppm (2q, 1H), 4.21–4.05 ppm (m, 4H), 1.73 ppm and 1.72 ppm (2d, 3H), 1.45 ppm and 1.42 ppm (2q, 3H), 1.36–1.26 ppm (m, 6H).

EXAMPLE 7

A solution of 1.85 g of potassium 5-(o-chloro-p-trifluoromethyl-phenoxy)-2-nitrophenolate and 1.29 g of 3-diethylphosphopropyl bromide in 25 ml of abosulte dimethyl sulfoxide is heated at 75°–80° C. for 4 hours. Most of the solvent is thereafter distilled off under reduced pressure, the residue is treated with water and the aqueous solution is brought to pH-value of about 6. The aqueous solution is subsequently shaken out with ethyl acetate, and the combined organic extracts are washed with water, dried over anhydrous sodium sulphate and evaporated to dryness. The residue is purified by chromatography on silica gel with n-hexane/ethyl acetate followed by pure ethyl acetate as the eluant. There is obtained diethyl 3-[5-o-chloro-p-trifluoromethylphenoxy)-2-nitrophenoxy]-propylphosphonate, ¹H-NMR (CDCl₃; 400 MHz) 7.95 ppm (d, 1H), 7.80 ppm (d, 1H), 7.58 ppm (q, 1H), 7.20 ppm (d, 1H), 6.69 ppm (d, 1H), 6.45 ppm (q, 1H), 4.11 ppm (m, 6H), 2.17 ppm (m, 2H), 1.02 ppm (m, 2H), 1.32 ppm (tt, 6H).

In an analogous manner, by using potassium 5-(o-chloro-p-trifluoromethyl-phenoxy)-2-nitrophenolate and 2-isopropylideneaminooxy-ethyl 2-bromopropionate there is obtained 2-isopropylidene-aminooxy-ethyl 2-[5-o-chloro-p-trifluoromethyl-phenoxy)-2-nitrophenoxy]-propionate, ¹H-NMR (CDCl₃; 400 MHz) 7.93 ppm (d, 1H), 7.70 ppm (d, 1H), 7.58 ppm (q, 1H), 7.18 ppm (d, 1H), 6.59 (d, 1H), 6.49 ppm (q, 1H), 4.81 ppm (q, 1H), 4.37 ppm (m, 2H), 4.15 ppm (t, 2H), 1.84 ppm (s, 3H), 1.79 ppm (s, 3H), 1.71 ppm (d, 3H);

by using potassium 5-(o-chloro-p-trifluoromethyl-phenoxy)-2-nitrophenolate and diethyl (2-bromopropionyloxy)-methylphosphonate there is obtained diethyl [2-[5-(o-chloro-p-trifluoromethyl-phenoxy)-2-nitrophenoxy]-propionyloxy]methylphosphonate, ¹H-NMR (CDCl₃; 400 MHz) 7.93 ppm (d, 1H), 7.79 ppm (d, 1H), 7.58 ppm (q, 1H), 7.21 ppm (d, 1H), 6.63 ppm (d, 1H), 6.49 ppm (q, 1H), 4.89 ppm (q, 1H), 4.45 ppm (m, 2H), 4.14 ppm (m, 4H), 1.74 ppm (d, 3H), 1.32 ppm (tt, 6H).

EXAMPLE 8

A solution of 2.0 g of 2-[5-(o-chloro-p-trifluoromethyl-phenoxy)-2-nitrophenoxy]-propionic acid in 20 ml of dimethylformamide is added dropwise to 0.22 g of a 55% dispersion of sodium hydride in oil. The mixture is subsequently heated to 50° C. and stirred for 15 minutes. A solution of 1.3 g of diethyl 3-bromopropylphosphonate in 4 ml of dimethylformamide is then added thereto and the reaction mixture is stirred at 50° C. for 6 hours.

For the working-up, most of the solvent is distilled off under reduced pressure, the residue is dissolved in ethyl acetate, and the solution is washed with water, dried over anhydrous sodium sulphate and evaporated. The crude produce is finally purified by chromatography on silica gel with ethyl acetate/n-hexane (3:1). There is obtained diethyl 3-[2-[5-(o-chloro-p-trifluoromethyl-phenoxy)-2-nitrophenoxy]-propionyloxy]-propylphosphonate, $^1$N-NMR (CDCl$_3$, 400 MHz), 7.93 ppm (d, 1H), 7.79 ppm (d, 1H), 7.60 ppm (q, 1H), 7.23 ppm (d, 1H), 6.57 ppm (d, 1H), 6.50 ppm (q, 1H), 4.81 ppm (q, 1H), 4.28–4.00 ppm (m, 6H), 1.99–1.86 ppm (m, 2H), 1.76–1.65 ppm (m, 5H), 1.36–1.27 ppm (2 x tt, 6H).

EXAMPLE 9

2.76 g of anhydrous potassium carbonate and 3.78 g of 2-isopropylideneaminooxy-ethyl 2-bromopropionate are added to a solution of 2.89 g of 3-(o-chloro-p-trifluoromethyl-phenoxy)-phenol in 40 ml of acetone and the mixture is heated at reflux temperature for 6 hours. The resulting solution is then concentrated to 30 ml and the concentrate is poured into 100 ml of water. The mixture is extracted three times with 80 ml of ethyl acetate each time, the combined organic phases are back-washed twice with 50 ml of water each time, the solvent is evaporated from the organic phase and there is obtained by distillation in a bulb-tube at 100°–170° C./0.05 mm Hg 2-isopropylideneaminooxy-ethyl 2-[3-(o-chloro-p-trifluoromethyl-phenoxy)-phenoxy]-propionate.

2.3 g of the product of the first reaction step are dissolved in 8 ml of acetic anhydride and treated with 0.6 g of copper nitrate trihydrate in 4 ml of acetic anhydride. The resulting solution is stirred at 45° C. for 12 hours, treated with a further 0.3 g of copper nitrate trihydrate and stirred for a further 25 hours. The reaction mixture is then poured on to 50 g of ice/water and the aqueous mixture is extracted three times with 50 ml of ethyl acetate each time. The combined organic phases are washed netural, concentrated and the oily residue is chromatographed on a hundred-fold amount of silica gel G with n-hexane/ethyl acetate (4:1). After evaporation of the solvent 2-isopropylideneaminooxy-ethyl 2-[5-(o-chloro-p-trifluoromethyl-phenoxy)-2-nitrophenoxy]-propionate is isolated in the form of an oil, $^1$H-NMR (CDCl$_3$, 60 MHz) 8.05–6.40 ppm (several signals, 6H), 4.85 ppm (q, 1H), 4.31 ppm (m, 4H), 1.82 ppm (s, 3H), 1.78 ppm (s,3H), 1.72 ppm (d, 3H). This product is also chromatographically identical with the second end product of Example 7.

EXAMPLE 10

A solution of 1.89 g of 2-isopropylideneaminooxyethyl 2-hydroxypropionate in 5 ml of absolute dioxan in added dropwise during 15 minutes at 25°–30° C. to 0.48 g of a 55% oil dispeson of sodium hydride in 10 ml of absolute dioxan and the mixture is stirred for 30 minutes. A solution of 3.62 g of 2-chloro-4-trifluoromethylphenyl 3,4-dinitrophenyl ether in 10 ml of absolute dioxan is subsequently added dropwise during 10 minutes, the temperature thereby rising to 30° C.

The reaction mixture is stirred at room temperature for 1 hour and the solvent is distilled off in vacuo. The residue is dissolved in diethyl ether, washed neutral with water, dried over anhydrous sodium sulphate and evaporated to dryness. The crude product is finally purified by chromatography on silica gel with ethyl acetate/n-hexane (1:5). There is obtained 2-isopropylideneaminooxy-ethyl 2-[5-(-o-chloro-p-trifluoromethylphenoxy)-2-nitrophenoxy]-propionate, $^1$H-NMR (CDCl$_3$, 400 MHz) 7.93 ppm (d, 1H), 7.79 ppm (d, 1H), 7.58 ppm (q, 1H), 7.18 ppm (d, 1H), 6.59 ppm (d, 1H), 6.49 ppm (q, 1H), 4.81 ppm (q, 1H), 4.37 ppm (m, 2H), 4.15 ppm (t, 2H), 1.84 ppm (s, 3H), 1.79 ppm (s, 3H), 1.71 ppm (d, 3H).

II.

Preparation of the starting materials

EXAMPLE 11

The carbamic acid esters used as starting materials in Examples 4 and 9 can be produced as follows:

A solution of 32.4 g of 2-bromopropionyl bromide in 70 ml of diethyl ether is added dropwise within one hour while cooling with ice to a solution, cooled to 0° C., of ethyl 2-hyroxyethylcarbamate and 13.1 g of pyridine in 80 ml of diethyl ether. The reaction mixture is then stirred at room temperature for 45 minutes. For the working-up, the mxture is filtered under suction through Celite and the filtrate is poured into water. The aqeuous phase is extracted twice with diethyl ether, and the combined organic phases are washed twice with water and once with saturated sodium chloride solution, dried over anhydrous sodium sulphate and evaporated to dryness. There is obtained ethyl 2-(2-bromopropionyloxy)-ethylcarbamate as a colourless oil which either can be used in the reaction without further purification or can be purified further by chromatography on silica gel with n-hexane/diethyl ether (1:1); $n_D^{20}$ 1.4770.

In an analogous manner, by using methyl 2-hydroxyethylcarbamate and 2-bromopropionyl bromide there is obtained methyl 2-(2-bromopropionyloxy)-ethylcarbamate, $n_D^{20}$ 1.4779;

by using ethyl 2-hydroxyethylcarbamate and bromoacetyl bromide there is obtained ethyl 2-bromoacetoxy-ethylcarbamate, $n_D^{20}$ 1.4853;

by using methyl 2-hydroxyethylcarbamate and bromoacetyl bromide there is obtained methyl 2-bromoacetoxyethylcarbamate, $n_D^{20}$ 1.4891;

by using ethyl 1-ethyl-2-hydroxy-ethylcarbamate and 2-bromopropionyl bromide there is obtained ethyl 1-ethyl-2-(2-bromopropionyloxy)-ethylcarbamate, $n_D^{20}$ 1.4736;

by using isobutyl 2-hydroxyethylcarbamate and 2-bromopropionyl bromide there is obtained isobutyl 2-(2-bromopropionyloxy)-ethylcarbamate, $n_D^{20}$ 1.4731;

by using methyl 2-hydroxypropylcarbamate and 2-bromopropionyl bromide there is obtained methyl 2-(2-bromopropionyloxy)-propylcarbamate, $n_D^{20}$ 1.4764;

by using methyl N-(2-hydroxyethyl)-N-methyl-carbamate and 2-bromopropionyl bromide there is obtained methyl N-[2-(2-bromopropionyloxy)-ethyl]-N-methyl-carbamate, $^1$H-NMR (CDCl$_3$, 60 MHz) 4.35 ppm (q, 1H), 4.32 ppm (t, 2H), 3.75 ppm (s, 3H), 3.58 ppm (t, 2H), 3.0 ppm (s, 3H), 1.82 ppm (d, 3H);

by using 2-isopropylideneaminooxy-ethanol and 2-bromopropionyl bromide there is obtained 2-isopropylideneaminooxy-ethyl 2-bromopropionate, $n_D^{20}$ 1.4710.

EXAMPLE 12

The D-2-[5-(2-chloro-p-trifluoromethyl-phenoxy)-2-nitrophenoxy]-propionic acid used as the starting material in Example 5 can be produced as follows:

2.0 g of 5-(o-chloro-p-trifluoromethyl-phenoxy)-2-nitrophenol and 1 g of potassium carbonate are heated at reflux temperature for 30 minutes in 30 ml of acetonitrile. 1.8 g of ethyl L-2-tosyloxypropionate are subsequently added dropwise to the warm mixture, and the mixture is left to react at reflux temperature for 1.5 hours. For the working-up, the mixture is poured on to ice-water and the aqueous phase is extracted twice with diethyl ether. The combined organic phases are then washed with 2N hydrochloric acid, water and saturated sodium chloride solution, dried over anhydrous sodium sulphate and evaporated to dryness. The residue is purified by chromatography on silica gel using n-hexane/ethyl acetate (9:1) as the eluent. There is obtained ethyl D-2-[5-(o-chloro-p-trifluoromethyl-phenoxy)-2-nitrophenoxy]-propionate $[\alpha]_D^{22} -39.26°$ (c=0.98% in CHCl$_3$); $^1$H-NMR (CDCl$_3$, 60 MHz) 8.1–6.46 ppm (m, 6H), 4.8 ppm (q, 1H), 4.22 ppm (q, 2H), 1.70 ppm (d, 3H), 1.23 ppm (t, 3H).

From the above product there is obtained by saponification with potassium hydroxide in methanol/water at room temperature D-2-[5-(o-chloro-p-trifluoromethyl-phenoxy)-2-nitrophenoxy]-propionic acid, $[\alpha]_D^{22} -19.25°$ (c=1.04% in CHCl$_3$).

III.

Formulation Example

EXAMPLE 13

For the manufacture of an emulsifiable concentrate the ingredients listed hereinafter are mixed with one another;

Compound of formula I: 250 g/l
Nonylphenol-(10)-ethoxylate: 50 g/l
Calcium dodecylbenzenesulphonate: 25 g/l
Solvent mixture of alkylbenzenes: to 1000 ml The thus-obtained concentrate emulsifies spontaneously in water. The emulsion formed is suitable as a ready-for-use spray liquor

IV.

Preparation of an active ingredient compound of formula I

EXAMPLE 14

Preparation of 2-[(isopropylideneamino)oxy]-ethyl D,L-2-{5-[(2-chloro-α,α,α-trifluoro-p-tolyl)oxy]-2-cyano-phenoxy}-propionate To a suspension of 19.2 g of sodium hydride in 400 ml of dimethyl sulphoxide is added dropwise a solution of 54.0 g of 2,4-dihydroxybenzonitrile in 200 ml of dimethyl sulphoxide. After formation of the sodium salt 86.0 g of 3,4-dichloro-α,α,α-trifluorotoluene and 0.1 g of copper powder are added and the reaction mixture is stirred at 115° C. for 68 hours. Then the mixture is poured onto 2 kg of ice and the aqueous mixture acidified with concentrated hydrochloric acid and extracted severl times with 500 ml portions of ethyl acetate. The combined organic phases are neutralized and dried over anhydrous sodium sulphate, and the solvent is evaporated off under reduced pressure. Finally, the residue is prified by column chromatographyon silica gel using ethyl acetate / n-hexane (7:3) as the eluent and crystallized from methylene chloride. There is obtained the intermediate 4-[(2-chloro-α,α,α-trifluoro-p-tolyl)oxy]-salicylonitrile, m.p. 155°–156° C.; mass spectrum; m/e 313, 294, 278, 250,223, 209, 90, 63; infrared spectrum: main peak at 2230 cm$^{-1}$.

15.68 g of this intermediate, 13.86 g of 2-[(isopropylideneamino)oxy]-ethyl D,L-2-bromopropionate and 13.81 g of potassium carbonate are suspended in 200 ml of acetone and the suspension is stirred at reflux temperature for 19 hours. Subsequently, the solvent is evaporated off under reduced pressure, the residue is dissolved in 50 ml of water and the aqueous solution is extracted with three 50 ml portions of ethyl acetate. The combined organic phases are neutralized and dried over anhydrous sodium sulphate, and the solvent is then evaporated off under reduced pressure. Finally, the residue is purified by column chromatography on silica gel using ethyl acetate / n-hexane (4:1) as the eluent. The product, 2-[(isopropylideneamino)oxy]-ethyl D,L-2-{5-[(2-chloro-α,-trifluoro-p-tolyl)oxy]-2-cyano-phenoxy}-propionate, is isolated as a colourless oil, mass spectrum: m/e 484, 412, 340, 100, 56; infrared spectrum: main peaks at 2230 cm$^-$, 1740 cm$^{-1}$; $^1$H-NMR (60 MHz, CDCl$_3$): 7.9–6.5 ppm (m, 6H), 4.85 ppm (q, j=7Hz, 1H), 4.3 ppm (m, 4H), 1.85 ppm and 1.80 ppm (2 x s, 6H), 1.7 ppm (d, j=7Hz, 3H).

We claim:

1. A compound of the formula

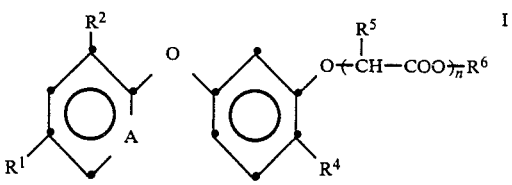

wherein
A is CR$^3$ or N,
R$^1$ is halogen or trifluoromethyl,
R$^2$ and R$^3$ independently of each other are hydrogen, halogen, nitro or cyano,
R$^4$ is halogen, nitro or cyano,
R$^5$ is hydrogen or C$_{1-3}$-alkyl,
n is 0 or 1,
R$^6$ is one of the following groups
(a)–(b)

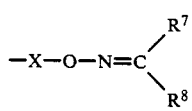

-continued

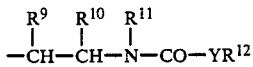

R⁷ is $C_{1-6}$-alkyl,

R⁸ is $C_{1-6}$-alkyl or $C_{1-6}$-alkoxy,

R⁷ and R⁸ together with the carbon atom to which they are attached are a $C_{5-7}$-cycloalkane ring, X is methylene, ethylene or ethylidene, R⁹ and R¹⁰ independently of each other are hydrogen or $C_{1-4}$-alkyl, R¹¹ is hydrogen or methyl, R¹² is $C_{1-4}$-alkyl or Z-chloroethyl, and Y is oxygen or sulphur.

2. The compound according to claim 1, wherein A is CH.

3. The compound according to claim 2, wherein R¹ is trifluoromethyl.

4. The compound according to claim 3, wherein R² is chlorine.

5. The compound according to claim 4, wherein R⁴ is nitro.

6. The compound according to claim 5, wherein R⁵ are hydrogen or methyl.

7. The compound according to claim 6, wherein R⁷ and R⁸ independently of each other are methyl or ethyl.

8. The compound according to claim 1, where A is CH, R¹ is trifluoromethyl, R² is halogen, R⁴ is halogen or nitro, R⁷ and R⁸ independently of each other are $C_{1-6}$-alkyl, R¹² is $C_{1-4}$-alkyl and Y is oxygen.

9. The compound according to claim 1 which is isopropylideneaminooxymethyl 2-[5-(o-chloro-p-trifluoromethyl-phenoxy)-2-nitrophenoxy]-propionate.

10. The compound according to claim 1 which is 2-isopropylideneaminooxy-ethyl 2-[5-(o-chloro-p-trifluoromethyl-phenoxy)-2-nitrophenoxy]-propionate.

11. The compound according to claim 1 which is methyl N-{[2-[5-(o-chloro-p-trifluoromethyl-phenoxy)-2-nitrophenoxy]-propionyloxy]-ethyl}-N-methyl-carbamate.

12. The compound according to claim 1 selected from the group consisting of:
2-Propanone O-[[5-(o-chloro-p-trifluoromethyl-phenoxy)-2-nitrophenoxy]methyl]oxime.
methyl 2-[5-(o-chloro-p-trifluoromethyl-phenoxy)-2-nitrophenoxy]-ethylcarbamate,
ethyl 2-[5-(o-chloro-p-trifluoromethyl-phenoxy)-2-nitrophenoxy]-ethylcarbamate,
methyl 2-[2-[5-(o-chloro-p-trifluoromethyl-phenoxy)-2-nitrophenoxy]-propionyloxy]-ethylcarbamate,
ethyl 2-[2-[5-(o-chloro-p-trifluoromethyl-phenoxy)-2-nitrophenoxy]-propionyloxy]-ethylcarbamate,
methyl 2-[[5-(o-chloro-p-trifluoromethyl-phenoxy)-2-nitrophenoxy]acetoxy]-ethylcarbamate,
ethyl 2-[[5-(o-chloro-p-trifluoromethyl-phenoxy)-2-nitrophenoxy]acetoxy]-ethylcarbamate,
methyl 2-[2-[5-(o-chloro-p-trifluoromethyl-phenoxy)-2-nitrophenoxy]-propionyloxy]-propylcarbamate,
ethyl 1-ethyl-2-[2-[5-(o-chloro-p-trifluoromethyl-phenoxy)-2-nitrophenoxy]-propionyloxy]-ethylcarbamate,
isobutyl 2-[2-[5-(o-chloro-p-trifluoromethyl-phenoxy)-2-nitrophenoxy]-propionyloxy]-ethylcarbamate,
ethyl 2-[D-2-[5-(o-chloro-p-trifluoromethyl-phenoxy)-2-nitrophenoxy]-propionyloxy]-ethylcarbamate,
methyl 2-[D-2-[5-(o-chloro-p-trifluoromethyl-phenoxy)-2-nitrophenoxy]-propionyloxy]-ethylcarbamate.

13. The compound according to claim 1, selected from the group consisting of:
Methyl 2-[2-[5-(o-chloro-p-trifluoromethyl-phenoxy-2-chlorophenoxy]-propionyloxy]-ethylcarbamate,
ethyl 2-[2-[5-(o-chloro-p trifluoromethyl-phenoxy-2-chlorophenoxy]-propionyloxy]-ethylcarbamate and
2-isopropylideneaminooxy-ethyl 2-[5-(o-chloro-p-trifluoromethyl-phenoxy-2-chlorophenoxy]-propionate.

14. A herbicidal composition which comprises inert carrier material and, as the active ingredient, an amount of a compound of claim 1 which is effective as a herbicide.

15. The herbicidal composition according to claim 14, which comprises an effective amount of isopropylideneaminooxymethyl 2-[5-(o-chloro-p-trifluoromethyl-phenoxy)-2-nitrophenoxy]-propionate or 2-isopropylideneaminooxy-ethyl 2-[5-(o-chloro-p-trifluoromethyl-phenoxy)-2-nitro-phenoxy]-propionate or methyl N-{2-[2-[5-(o-chloro-p-trifluoromethylphenoxy-2-nitrophenoxy]-propionyloxy]-ethyl}-N-methylcarbamate.

16. A herbicidal composition which comprises inert carrier material and, as the active ingredient, an amount of a compound of claim 7 which is effective as a herbicide.

17. A herbicidal composition which comprises inert carrier material and, as the active ingredient, an amount of a compound of claim 8 which is effective as a herbicide.

18. A herbicidal composition which comprises inert carrier material and, as the active ingredient, an amount of a compound of claim 9 which is effective as a herbicide.

19. A herbicidal composition which comprises inert carrier material and, as the active ingredient, an amount of a compound of claim 10 which is effective as a herbicide.

20. A herbicidal composition which comprises inert carrier material and, as the active ingredient, an amount of a compound of claim 11 which is effective as a herbicide.

21. A herbicidal composition which comprises inert carrier material and, as the active ingredient, an amount of a compound of claim 12 which is effective as a herbicide.

22. A herbicidal composition which comprises inert carrier material and, as the active ingredient, an amount of a compound of claim 13 which is effective as a herbicide.

23. The method for combatting weeds which comprises applying to the locus to be protected, a herbicidally effective amount of the compound of claim 1.

24. The method for combatting weeds which comprises applying to the locus to be protected, a herbicidally effective amount of the composition of claim 14.

25. A method for combatting weeds which comprises applying to the locus to be protected, a herbicidally effective amount of the composition of claim 15.

26. A method for combatting weeds which comprises applying to the locus to be protected, a herbicidally effective amount of the composition of claim 16.

27. The method for combatting weeds which comprises applying to the locus to be protected, a herbicidally effective amount of the composition of claim 17.

28. A method for combatting weeds which comprises applying to the locus to be protected, a herbicidally effective amount of the composition of claim 18.

29. A method for combatting weeds which comprises applying to the locus to be protected, a herbicidally effective amount of the composition of claim 19.

30. The method for combatting weeds which comprises applying to the locus to be protected, a herbicidally effective amount of the composition of claim 20.

31. A method for combatting weeds which comprises applying to the locus to be protected, a herbicidally effective amount of the composition of claim 21.

32. A method for combatting weeds which comprises applying to the locus to be protected, a herbicidally effective amount of the composition of claim 22.

33. The compound according to claim 1 which is 2-[(isopropylideneamino)oxy]-ethyl D,L-2-{5-[(2-chloro-$\alpha,\alpha,\alpha$-trifluoro-p-tolyol)oxy]-2-cyanophenoxy}-propionate.

34. A herbicidal composition which comprises inert carrier material and, as the active ingredient, an amount of a compound of claim 33 which is effective as a herbicide.

35. A method for combatting weeds which comprises applying to the locus to be protected a herbicidally effective amount of the composition of claim 34.

* * * * *